United States Patent [19]

Ikada et al.

[11] Patent Number: 5,250,584
[45] Date of Patent: Oct. 5, 1993

[54] PERIODONTIUM-REGENERATIVE MATERIALS

[75] Inventors: Yoshito Ikada, Uji; Shokyu Gen, Kyoto, both of Japan

[73] Assignee: G-C Dental Industrial Corp., Tokyo, Japan

[21] Appl. No.: 915,770

[22] Filed: Jul. 21, 1992

Related U.S. Application Data

[63] Continuation of Ser. No. 707,940, May 28, 1991, abandoned, which is a continuation of Ser. No. 566,896, Aug. 14, 1990, abandoned, which is a continuation of Ser. No. 391,922, Aug. 10, 1989, abandoned.

[30] Foreign Application Priority Data

Aug. 31, 1988 [JP] Japan .................. 63-214835

[51] Int. Cl.⁵ .................. A61F 2/00; C08G 63/08
[52] U.S. Cl. .................. 523/114; 523/115; 528/354; 528/361; 623/16
[58] Field of Search .................. 528/354, 361, 182; 435/240.3, 240.31; 433/229; 523/113, 114, 118, 115; 424/425, 426, 492; 623/16

[56] References Cited

U.S. PATENT DOCUMENTS

| | | | |
|---|---|---|---|
| 3,696,956 | 1/1972 | Schneider | 528/354 X |
| 3,839,297 | 10/1974 | Wasserman et al. | 528/354 X |
| 4,045,418 | 8/1977 | Sinclair | 528/354 X |
| 4,057,537 | 11/1977 | Sinclair | 528/354 |
| 4,471,077 | 9/1984 | Lange | 521/64 |
| 4,595,713 | 6/1986 | St. John | 528/354 X |
| 4,603,695 | 8/1986 | Ikada et al. | |
| 4,645,664 | 2/1987 | Lange | 528/354 X |
| 4,683,288 | 7/1987 | Tanaka et al. | 528/354 X |
| 4,758,435 | 7/1988 | Schaaf | 424/425 |
| 4,766,182 | 8/1988 | Murdoch et al. | 521/182 X |
| 4,818,542 | 4/1989 | De Luca et al. | 424/492 X |
| 4,832,686 | 5/1989 | Anderson | 424/426 X |

FOREIGN PATENT DOCUMENTS

| | | |
|---|---|---|
| 0058481 | 8/1982 | European Pat. Off. |
| 107591 | 5/1984 | European Pat. Off. |
| 0297535 | 1/1989 | European Pat. Off. |
| 7805831-0 | 5/1986 | Sweden |
| 1332505 | 10/1970 | United Kingdom |
| 1416196 | 12/1975 | United Kingdom |
| 2008135 | 5/1979 | United Kingdom |
| 2127839 | 4/1984 | United Kingdom |

OTHER PUBLICATIONS

Chemical Abstracts 99, 58873x (1983).
Chemical Abstracts 107, 238304e (1987).
Chemical Abstracts 107, 238305f (1987).
Chemical Abstracts 109, 237077n (1988).
I. Magnusson et al., "New Attachment Formation Following Controlled Tissue Regeneration Using Biodegradable Membranes*", *J. Periodontol*, Jan. 1988, pp. 1–6.

*Primary Examiner*—John Kight, III
*Assistant Examiner*—Shelley A. Dodson
*Attorney, Agent, or Firm*—Oblon, Spivak, McClelland, Maier & Neustadt

[57] ABSTRACT

A periodontium-regenerating material for the regenerative treatment of the periodontium consists of biodegradable/absorable copolymers of lactide/ε-caprolactone or lactide/glycolide having a weight-average molecular weight of 40,000 to 500,000 as well as a dynamic modulus of $5 \times 10^7$ to $5 \times 10^9$ dynes/cm² and a elongation rate of 100 to 2,000 %, both measured at room temperature (25° C.). Those copolymers may be used in the form of a sheet or film which may or may not be porous.

1 Claim, 3 Drawing Sheets

PERIODONTIUM-REGENERATIVE MATERIALS

This application is a continuation application of Ser. No. 07/707,940 filed May 28, 1991, which is a continuation application of Ser. No. 07/566,896 filed Aug. 14, 1990, which is a continuation application of Ser. No. 07/391,922 filed Aug. 10, 1989, now all abandoned.

BACKGROUND OF THE INVENTION

1. Field of the Invention

The present invention relates to a bio-degradable/absorbable dental material required for the regeneration of the tissues of a living body attacked by periodontosis.

2. Statement of the Prior Art

In current periodontal treatments of healthy cementum and periodontal ligament attacked by periodontal diseases, hydroxyapatite and calcium phosphate are used as the alveolar bone fillers to be filled in lost periodontal tissues.

However, such treatments are considered to be only effective to prevent periodontal diseases from reaching an advanced stage or recurring to some degrees. In recent years, the Guided Tissue Regeneration Technic developed by Professor S. Nyman et al (University of Gothenburg) from a biological standpoint of view has attracted attention in dental fields. For such epoch-making Guided Tissue Regeneration Technic, it has been reported that certain results are achievable with what is called Goretex membrane which is neither degradable nor absorbable in a living body. See S. Nyman et al, "The regenerative potential of the periodontal ligament—An experimental study in the monkey", J. Clin. Periodontol, 9:257, 1982.

Since Goretex membrane is neither degradable nor absorbable in a living body, it constitutes an alien substance to the living body and is reactive to the tissues. Therefore we must take off Goretex membrane after first treatment and second operation is thus again needed. From such a standpoint of view, a report of the studies of using bio-degradable/absorbable membranes for the Guided Tissue Regeneration Technic has been presented. See I. Magnusson et al, "New Attachment Formation Following Controlled Tissue Regeneration Using Biodegradable Membranes", J. Periodontol, 59, 1-6, January, 1988.

However, since a homopolymer consisting of 100% polylactic acid is used as the bio-degradable/absorbable membrane, it is impossible to control both dynamic (or mechanical) properties and a rate of hydrolysis simultaneously.

Due to its glass transition temperature higher than a temperature of a body, the homopolymer consisting of 100% polylactic acid gives a physical stimulus to the soft tissues of a living body with the resulting inducement of inflammation. With the homopolymer, it is difficult to freely vary the rate of hydrolysis.

The present inventors have made intensive and extensive studies to eliminate the weak points of the above homopolymer of polylactic acid, i.e., to improve especially its dynamic (or mechanical) properties, thermal properties and the rate of hydrolysis. As a consequence, it has been found that a film or sheet of a lactide/ε-caprolactone or a glycolide copolymer is best-suited for the Guided Tissue Regeneration Technic. Thus, the present invention has been accomplished.

SUMMARY OF THE INVENTION

A novelty of the present invention resides in using a lactide/ε-caprolactone or a glycolide copolymer as the bio-degradable/absorbable high-molecular materials applied to the Guided Tissue Regeneration Technic to be effective to prevent periodontal diseases. Such bio-degradable/absorbable materials may be formed into films or sheets by dissolving the lactide/ε-caprolactone or lactide/glycolide copolymers in a solvent such as an organic solvent, e.g., methylene chloride, chloroform, dioxane, toluene, benzene, dimethylformamide or acetone and subjecting the resulting solutions to casting or hot pressing. In order to allow such films or sheets to transmit body fluids such as nourishment therethrough or give flexibility thereto, they may be made porous by stretching or freeze-drying treatment in benzene or dioxane solution.

The bio-degradable/absorbable high-molecular materials according to the present invention excel in not only flexibility but also biocompatibility. Thus, they tend to disappear immediately after a cure of injured sites with no fear of interfering with the bony ankylosis of the connective tissue separated from a surface of a root by discission or lesion. The reason why such excellent biocompatibility is obtained is that it is possible to use materials whose dynamic and thermal properties as well as the rate of hydrolysis can be varied by the copolymerization of lactide that is an aliphatic polyester with ε-caprolactone or glycolide used in suitable ratios and that the materials can be selected in application depending upon how much the injured sites are to be cured.

BRIEF DESCRIPTION OF THE DRAWINGS

The present invention will now be explained in more detail with reference to the accompanying drawings, which are given for the purpose of illustration alone and in which.

DETAILED DESCRIPTION OF THE INVENTION

The bio-degradable/absorbable high-molecular materials used in the present invention are widely distributed in the natural world and are a copolymer of lactide/ε-caprolactone or lactide/glycolide found in the bodies of animals. The composition and molecular weight of such a copolymer may be selected depending upon the mechanical properties and bio-degrading/absorbing rate of material suitable for the condition of a periodontal disease. The lactide/ε-caprolactone copolymers used in the present invention are synthesized according to the following scheme.

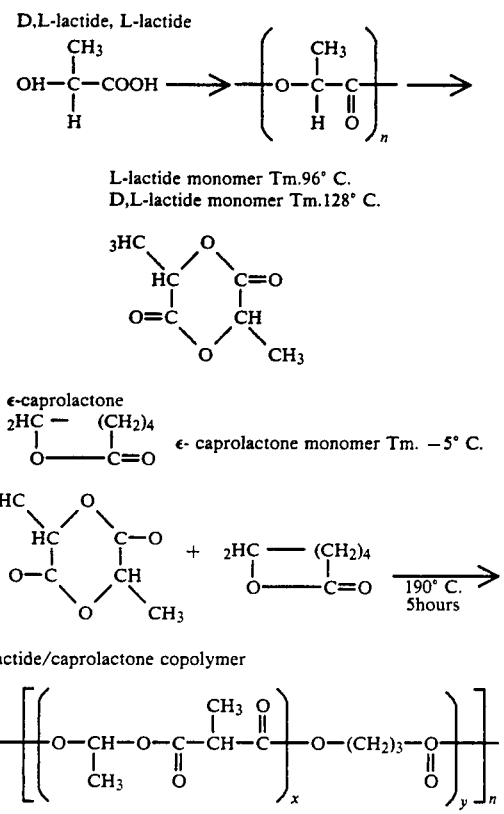

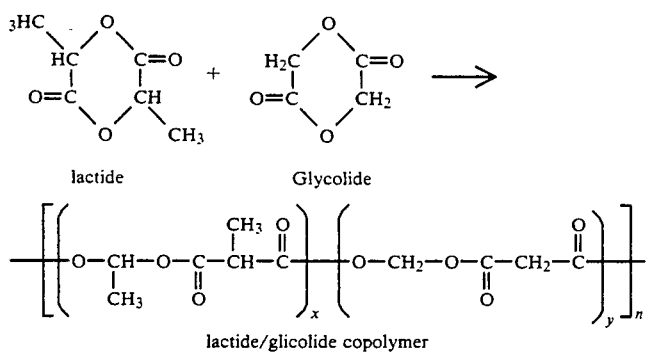

lactide/glicolide copolymer

Figure 1:
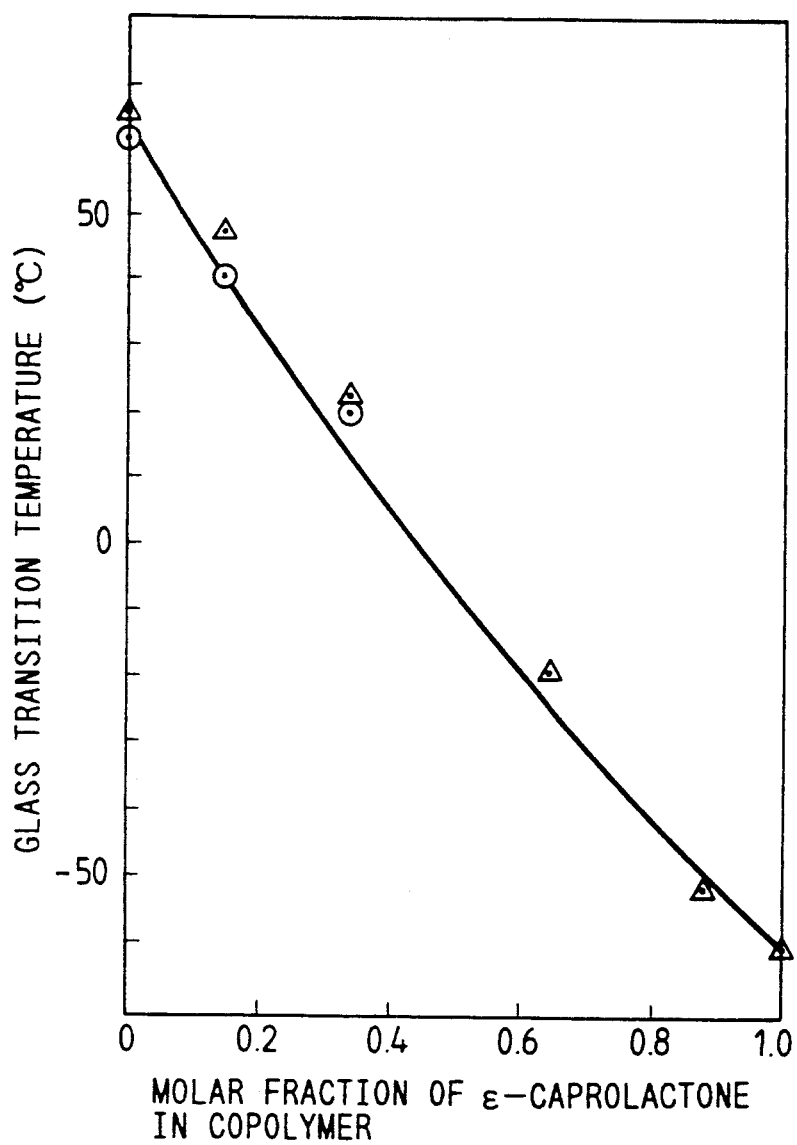
FIG. 1 is a graphical view showing the relation between the molar fraction of ε-caprolactone in the copolymer of L-lactide/ε-caprolactone and the glass transition temperature of that copolymer.

The bio-degradable/absorbable high-molecular materials used in the present invention come in touch with the soft tissues of a living body, and is thus required to have some flexibility, since inflammatory reactions are induced by physical stimuli at the time when there is a large difference between dynamic properties of such materials and those of the soft tissues of a living body, especially, when their hardness is in excess. In order to accomplish this aim, it is preferred that their glass transition temperature is in the vicinity of a temperature of a body. To meet such a requirement, it is required to select the composition of the lactide/ε-caprolactone or the lactide/glycolide copolymers according to suitable compositional ratios. FIG. 1 illustrates a change in the glass transition temperature on the molar fraction of ε-caprolactone in the copolymer of lactide/ε-caprolactone. It is understood that the measurement of glass transition temperature was carried out with a differential scanning calorimeter (DSC)—marked by Δ and a dynamic modulus meter—marked by ⊙.

Figure 2:
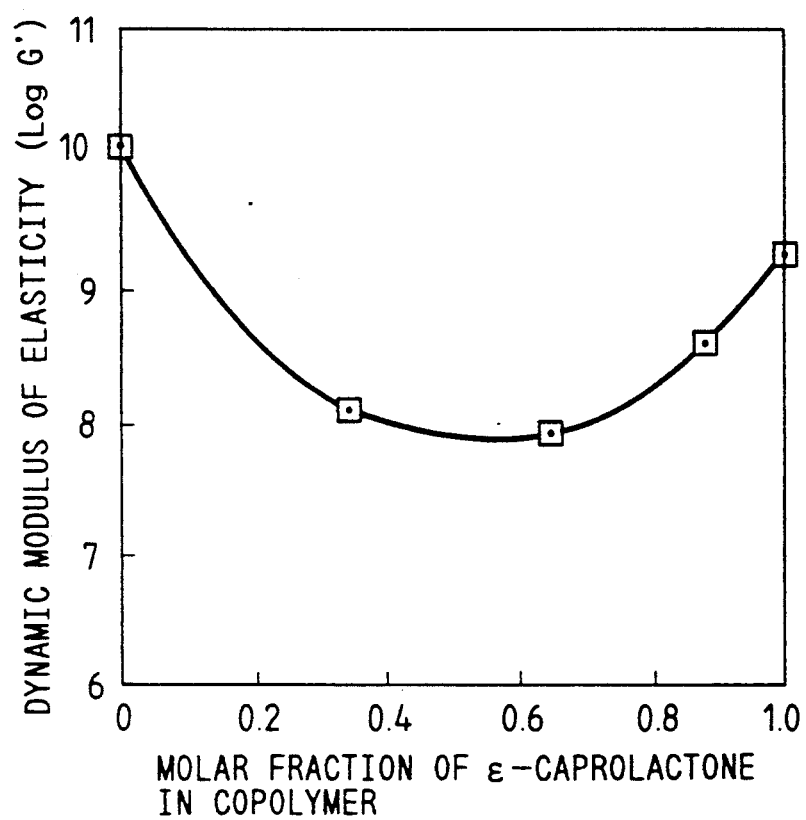
FIG. 2 is a graphical view illustrating the relation between the molar fraction of ε-caprolactone in the copolymer of L-lactide/ε-caprolactone and the dynamic modulus of elasticity thereof at room temperature.

The bio-degradable/absorbable high-molecular materials used in the present invention are required to have a certain dynamic strength. In other words, when there is a need of fixing the bio-degradable/absorbable films or sheets to a given region with a suture, a grave problem will arise if the fixed part tears up. In the absence of a certain strength or modulus of elasticity, on the other hand, it poses a problem in connection with the retainment of shape tending to change due to hydrolysis, so that the desired object cannot be attained. Therefore, the materials used in the present invention should preferably have a dynamic modulus in a range of $5 \times 10^7$ to $5 \times 10^9$ dynes/cm$^2$ that is attainable by the selection of the composition of the copolymers. FIG. 2 illustrates a change at room temperature in the dynamic modulus of elasticity on the molar fraction of ε-caprolactone in the copolymer of L-lactide/ε-caprolactone. It is understood that the dynamic modulus of elasticity was measured with Rheo-Vibron available from Toyo Balldwin, On the one hand, the bio-degradable/absorbable high-molecular materials used in the present invention should be retained in the form of a film or a sheet within a period during which the regeneration of the alveolar bone and the recombination of the surface of a root with the connective tissue are achieved. On the other hand, it is not desirable that they remain as an alien substance in a living body after curing. Thus, they are required to be rapidly degraded, absorbed and disappeared. The degradable/absorbable rate can also be controlled by varying a composition and a molecular weight of the copolymers.

Figure 3:
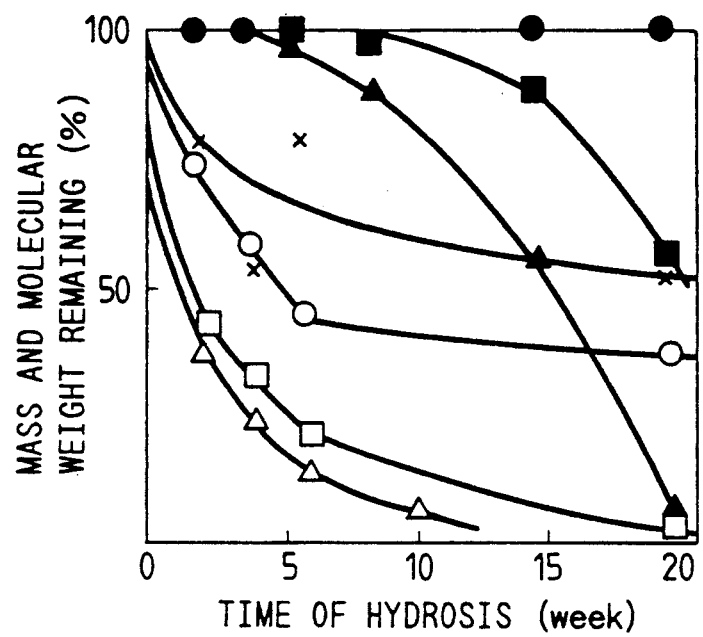
FIG. 3 is a graphical view showing the relation between the time of hydrolysis and the weight and rate of residual molecular weight of the copolymer of L-lactide/ε-caprolactone.
Figure 4:
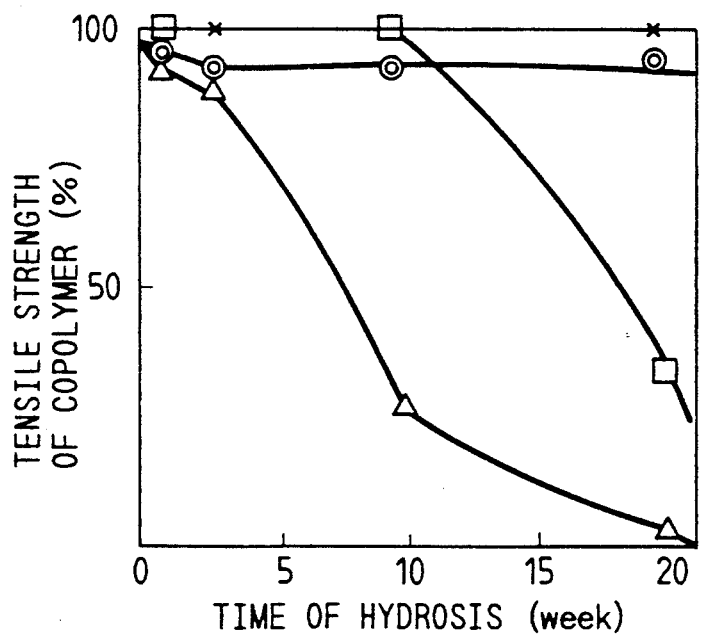
FIG. 4 is a graphical view showing the relation between the time of hydrolysis and the tensile strength of the copolymer of L-lactide/ε-caprolactone.

Changes in the in-vitro hydrolysis on the molar fraction of ε-caprolactone in the copolymer of L-lactide/ε-caprolactone therein are illustrated in FIGS. 3 and 4, wherein ○ stands for 100% L-lactide molecular weight, □ 88% L-lactide molecular weight, Δ 65% L-lactide molecular weight, ⊙ 15% L-lactide molecular weight, ×100% ε-caprolactone molecular weight, ● 100% L-lactide mass, ■ 88% L-lactide mass, and ▲ 65% L-lactide mass. The rate of hydrolysis of samples in the in-vitro were estimated in a solution having a certain volume (3 mm long×5 mm wide×1 mm thick) in a phosphate buffer solution of 37° C. (pH: 7.4) with an elution tester according to THE PHARMACOPOEIA OF JAPAN. The weight, molecular mass and the rate of reductions of tensile strength of the hydrolysated products were measured before and after hydrolysis and expressed in terms of percentage.

Then, the bio-degradable/absorbable rates and reactivity to a tissue were investigated by in-vivo tests. The dorsal muscles of house rabbits, each weighing about 3 kg, were incised along the fibrous direction, the samples were filled, and the fasciae were then sutured. Prior to the filling, the samples were sterilized with an ethylene oxide gas. After the filling, the rabbits were slaughtered with the lapse of time to examine changes in the physical properties of the samples and the reactivity of the peripheral tissues. As a consequence, the homopolymer consisting of 100% polylactic acid remained substantially in its entirety even after the lapse of six months and the soft tissue in touch with the periphery of the material suffered from some inflammation. However, the copolymers of lactide/$\epsilon$-caprolactone (at a molar ratio of 70:30 mol %) and lactide/glycolide (at a molar ratio of 75:25 mol %) were completely degraded and absorbed with no sign of any tissular reaction.

From the above results, it is appreciated that the copolymers of lactide/$\epsilon$-caprolactone and lactide/glycolide are superior to the homopolymer consisting of 100% polylactic acid in the dynamic properties and the rate of hydrolysis as well as the biocompatibility. The copolymers of lactide/$\epsilon$-caprolactone and lactide/glycolide are interesting materials since, as is the case with the homopolymer consisting of 100% polylactic acid, they cause non-enzymatical hydrolysis in a living body to give hydrolyzates which are degraded and absorbed and finally discharged from the living body in the form of water and carbon dioxide. Thus, the bio-degradable/absorbable high-molecular materials according to the present invention are not only useful materials for the Guided Tissue Regeneration Technic, but are also clinically useful materials in other dental fields.

The bio-degradable/absorbable high-molecular materials of the present invention will now be explained specifically but not exclusively with reference to the following examples.

EXAMPLE 1

A fully developed mongrel was forcedly made to suffer from a periodontal disease, thereby inducing gingival retraction. The bio-degradable/absorbable porous film was used in the form of an about 200 $\mu$m thick sheet consisting of a L-lactide/$\epsilon$-caprolactone copolymer (at a molar ratio of 70:30 mol %) having a weight-average molecular weight of about 220,000 as well as a dynamic modulus of elasticity of $9.5 \times 10^7$ dynes/cm$^2$ a tensile strength of 3.1 N/mm$^2$ and a elongation rate of 150%, both at room temperature (25° C.). After the surface of the root had been covered with such the sheet in a form of a patched tent, a flap of the gingival tissue was back-sutured to prevent the connective tissue from coming in contact with the surface of the root and taking part in the process of healing. After the lapse of three months, the process of healing was observed. As a result, the L-lactide/$\epsilon$-caprolactone copolymer was found to lose a substantial part of its dynamic strength and cause considerable hydrolysis, although its shape was remained. However, new attachment including a formation of the new alveolar bone indicated that the periodontal disease was cured.

EXAMPLE 2

As the bio-degradable/absorbable film, use was made of an about 180 $\mu$m thick film-like material consisting of a D,L-lactide/glycolide copolymer (at a molar ratio of 80:20 mol %) having a weight-average molecular weight of 170,000 as well as a dynamic modulus of elasticity $9.8 \times 10^7$ dynes/cm$^2$ a tensile strength of 4.8 N/mm$^2$ and a elongation rate of 200%, both at room temperature (25° C.). According to the procedures of Example 1, the process of healing was estimated after the lapse of three months. As a consequence, it was found that the film consisting of the D,L-lactide/glycolide copolymer was substantially degraded and absorbed, and that the periodontal ligament fibers were formed simultaneously with the formation of a new bone, a sign of healing of the periodontal disease.

EXAMPLE 3

A 10% dioxane solution of a L-lactide/glycolide copolymer (at a molar ratio of 90:10 mol %) having a weight-average molecular weight of about 260,000 as well as a dynamic modulus of elasticity of $1.8 \times 10^8$ dynes/cm$^2$ a tensile strength of 7.5 N/mm$^2$ and a elongation rate of 1000%, both at room temperature (25° C.) was freeze-dried to prepare a bio-degradable/absorbable porous film in the form of an about 220 $\mu$m sheet. With this film, an animal experiment was performed in a similar manner as described in Example 1. After the lapse of three months, it was found that the porous sheet-like film consisting of the L-lactide/glycolide copolymer was completely degraded and absorbed with a healing of periodontal disease.

EXAMPLE 4

A 10% dioxane solution of a D,L-lactide/glycolide copolymer (at a molar ratio of 75:25 mol%) having a weight-average molecular weight of about 190,000 as well as a dynamic modulus of elasticity of $3.2 \times 10^8$ dynes/cm$^2$ and a elongation rate of 1500%, both at room temperature (25° C.) was freeze-dried to prepare a bio-degradable/absorbable porous film in the form of an about 160 $\mu$m sheet. With this film, an animal experiment was performed in a similar manner as described in Example 1. After the lapse of three months, it was found that the porous sheet-like film consisting of the D,L-lactide/glycolide copolymer was completely degraded and absorbed with a healing of periodontal disease.

COMPARATIVE EXAMPLE 1

An experiment was performed according to Example 1, provided that an about 200 $\mu$m thick material consisting of polylactic acid having a molecular weight of about 220,000 was used as the bio-degradable/absorbable film, to observe the degree of healing after the lapse of three months. As a result, it was found that the polylactic acid film was not substantially degraded with the inducement of partial inflammation in the gingival tissue in touch with the edges of the film consisting of 100% polylactic acid.

The bio-degradable/absorbable high-molecular materials of the present invention have the following advantages in comparison with the high-molecular materials which are neither degradable nor absorbable in a living body.

According to the Guided Tissue Regeneration Technic proposed by Professor S. Nyman et al. (University of Gothenburg), it is essentially required to remove the material inplanted in the periodontium immediately after the periodontium are found to be healed by such inplant. For such removal, it is again necessary to perform an operation. With the bio-degradable/absorbable high-molecular materials of the present invention, however, it is unnecessary to perform a re-operation, thus easing a patient of pain and relieving an economical burden to a considerable degree.

The material inplanted in the periodontium is required to have strength at the beginning, but is rather needed to lose that strength after the healing of the periodontal disease. No change in strength tends to induce inflammation. However, the bio-degradable/absorbable high-molecular materials of the present invention have strength at the start, which can be decreased gradually or sharply with the lapse of time, and so there is no possibility of inducing inflammation in the periodontium.

Moreover, the bio-degradable/absorbable high-molecular materials of the present invention have the following advantages in comparison with those consisting of homopolymers of 100% polylactic acid.

The dynamic/mechanical properties suitable for the conditions of the periodontium can be given to the bio-degradable/absorbable high-molecular materials of the present invention because the materials consist of the copolymers of lactide/ε-caprolactone or lactide/-glycolide. It is required to vary the rates of bio-degradation and -absorption of the material inplanted in the periodontium depending upon the degree of periodontal disease. Especially when it is intended to decrease sharply the dynamic/mechanical properties of the bio-degradable/absorbable high-molecular materials at the time when a certain period of time elapses after its inplant in the periodontium, difficulty is involved in freely varying the rate of hydrolysis of the bio-degradable/absorbable high-molecular material consisting of the homopolymer of 100% polylactic acid. With the bio-degradable/absorbable high-molecular materials of the present invention, however, it is possible to freely control their rates of degradation and absorption.

Further, the bio-degradable/absorbable high-molecular materials of the present invention give little or no physical stimuli to the soft tissues of a living body because their glass transition temperature is in the vicinity of body heat in comparison with the bio-degradable/absorbable materials consisting of the homopolymer of 100% polylactic acid.

What is claimed is:

1. A periodontium-regenerating material consisting essentially of bio-degradable/absorbable high-molecular weight material of lactide/ε-caprolactone copolymer or a lactide/glycolide copolymer which is used for the regenerative treatment of the periodontium, said copolymer being in a form of a porous film or a sheet and having a weight-average molecular weight in the range of 40,000 to 500,000, a molar ratio in the range of 90:10 to 5:95 mol %, a thickness in the range of 10 to 500 μm, a dynamic modulus of elasticity in the range of $5 \times 10^7$ to $5 \times 10^9$ dynes/cm$^2$, a tensile strength of 3.1 N/mm$^2$ or greater, an elongation rate of 100 to 2,000% each measured at room temperature (25° C.), retention rate of tensile strength reduced to zero after a lapse of one to six months due to hydrolysis action in vitro measured in a phosphate buffer solution of 37° C. and pH 7.4; and the transistion temperature is below body temperature.

* * * * *